United States Patent [19]

Corriu et al.

[11] Patent Number: 4,665,209

[45] Date of Patent: May 12, 1987

[54] PROCESS FOR THE PREPARATION OF HYDROGENOSILANES OR HALOGENOSILANES

[75] Inventors: Robert J. Corriu; Geneviève E. Cerveau, both of Montpellier; Claude G. Chuit, Palavas les Flots; Catherine Reye, Montpellier, all of France

[73] Assignee: Centre National de la Recherche Scientifique, Paris, France

[21] Appl. No.: 813,739

[22] Filed: Dec. 24, 1985

[30] Foreign Application Priority Data

Dec. 27, 1984 [FR] France .............................. 84 19884

[51] Int. Cl.$^4$ ........................... C07F 7/08; C07F 7/18

[52] U.S. Cl. ..................................... 556/474; 556/477
[58] Field of Search ................................. 556/474, 477

[56] References Cited

U.S. PATENT DOCUMENTS 3,337,597  8/1967  Berger .................................. 556/474

Primary Examiner—Paul F. Shaver
Attorney, Agent, or Firm—Fulbright & Jaworski

[57] ABSTRACT

A process for the preparation of hydrogenosilanes or halogenosilanes corresponding to the general formula I:

$$R-SiR'_3$$

5 Claims, No Drawings

PROCESS FOR THE PREPARATION OF HYDROGENOSILANES OR HALOGENOSILANES

The present invention relates to the preparation of hydrogenosilanes or halogenosilanes corresponding to the general formula I:

$$R-SiR'_3 \quad (I)$$

in which:

R represents a hydrogen or chlorine atom or an alkyl, alkenyl, alkynyl, aryl, aralkyl, aralkenyl, aralkynyl or alkylaryl radical in which the aliphatic fragments are linear, branched or cyclic and contain from 1 to 20 carbon atoms, and R' represents a hydrogen or chlorine atom.

Throughout the present description, the aryl radicals and the aromatic fragments of the aralkyl, aralkenyl, aralkynyl and alkylaryl radicals denote phenyl and naphthyl radicals.

Silanes are usually prepared by heating elemental silicon with an alkyl or aryl halide in the presence of a copper-based catalyst. This type of direct synthesis reaction has the disadvantage that it most frequently leads to mixtures of various products. Thus, the reaction of silicon with methyl chloride produces a mixture of methylchlorosilanes according to the following reaction scheme:

$$CH_3Cl + Si \xrightarrow[300°C.]{Cu (10\%)} SiCl_4 + CH_3SiHCl_2 + CH_3SiCl_3 + (CH_3)_2SiCl_2$$

By contrast, the present invention makes it possible specifically to obtain a very wide variety of silanes with an excellent degree of purity and with excellent yields. The majority of such silanes are known and can be used, for example, as crosslinking agents in organopolysiloxane compositions.

The process of the invention comprises reacting a silicon complex corresponding to the general formula II:

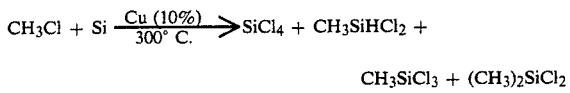

in which:

R represents an alkyl, alkenyl, alkynyl, aryl, aralkyl, aralkenyl, aralkynyl or alkylaryl radical in which the aliphatic fragments are linear, branched or cyclic and contain from 1 to 20 carbon atoms, A represents an alkali metal or alkaline earth metal, n=0 or 1 and a, b, x and y=1 or 2, with the proviso that:

when n=0, x=2 when n=1, x=1 and satisfying the equation of electrical neutrality:

$$ax = by,$$

with a reducing agent or a halogen-containing oxidizing agent in an anhydrous solvent medium and under an inert atmosphere, and then carrying out acid hydrolysis and extracting the said compound of the formula I.

In a particular method of carrying out the process of the invention, the starting silicon complex is a hexacoordinate complex of the general formula IIa:

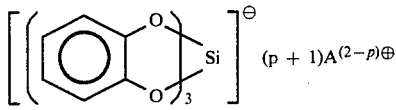

in which:

A represents an alkali metal or alkaline earth metal and p=0 or 1.

In another modified method of carrying out the process of the invention, the starting silicon complex is a pentacoordinate complex of the general formula IIb:

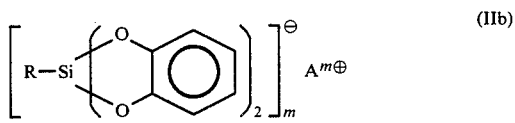

in which:

R denotes an alkyl, alkenyl, alkynyl, aryl, aralkyl, aralkenyl, aralkynyl or alkylaryl radical in which the aliphatic fragments are linear, branched or cyclic and contain from 1 to 20 carbon atoms, A represents an alkali metal or alkaline earth metal and m=1 or 2.

Each of these complexes of the formula IIa or IIb can be treated with a reducing agent chosen, for example, from hydrides, such as lithium aluminum hydride, diisobutylaluminum hydride and sodium hydride associated with a trialkylaluminum compound, especially triethylaluminum, to give a variety of trihydrogenosilanes or even silane itself, $SiH_4$.

Each of the complexes of the formula IIa or IIb can also be reacted with a halogen-containing oxidizing agent chosen from the group comprising chlorine, hydrochloric acid under pressure, $PCl_3$, $PCl_5$, $POCl_3$ and $SOCl_2$, to give a variety of halogenosilanes, in particular trichlorosilanes. By reacting the complex of the formula II with $PCl_5$, $SOCl_2$ or HCl under pressure, it is possible to obtain silicon tetrachloride.

The complexes of the general formula II can be prepared, for example, in the following manner

EXAMPLE 1

Preparation of sodium tris(benzene-1,2-diolato)silicate

The preparations are carried out under nitrogen in a Schlenk tube with degassed solvents in order to avoid oxidation of the sodium catecholate.

(a) starting from methyl silicate

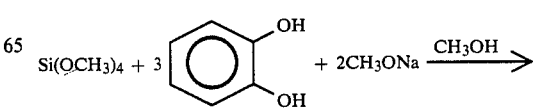

-continued

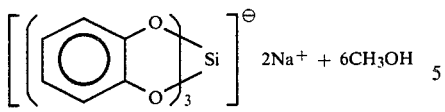

6.4 g (0.278 mol) of sodium are dissolved in 80 ml of methanol. A solution of 22.5 g (0.148 mol) of methyl silicate in 20 ml of methanol is then added, followed by a solution of 47.5 g (0.432 mol) of pyrocatechol in 50 ml of methanol. While the pyrocatechol is being introduced, the reaction mixture becomes milky and then homogeneous. It is heated for 1 hour at 60° C. The methanol is then driven off in vacuo and the complex is washed with ether to remove the excess methyl silicate and pyrocatechol. The complex is filtered off in air and washed twice with ether. It is dried in vacuo at 150° C. for 30 hours to remove all the ether (the ether is strongly adsorbed on the complex).

This gives 54.5 g (0.137 mol, 98%) of an amorphous, white air-stable powder which does not melt at 300° C. This complex is soluble in THF, methanol and pyridine and insoluble in the other customary solvents. Spectral characteristics (TMS standard): $^{13}C$ NMR $(CD_3OD)\delta=151.3$; 118.6; 111.7 ppm. $^{29}Si$ NMR $(CD_3OD)\delta=-113$ ppm.

(b) starting from silica

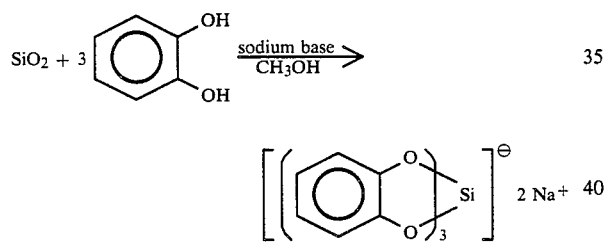

By using the same general conditions as in Example 1(a), but replacing the methyl silicate with silica or a silica gel, the same coordination complex is obtained, with a yield of 70%, by heating the reaction mixture for 18 hours at 60° C.

EXAMPLE 2

Preparation of lithium tris(benzene-1,2-diolato)silicate

By following the same procedure as in Examples 1(a) and 1(b), and using lithium methylate, the corresponding lithium complex is obtained. When starting from methyl silicate, the reaction yield is quantitative (95–100%).

EXAMPLE 3

Preparation of magnesium tris(benzene-1,2-diolato)silicate

By following the same procedure as in Examples 1(a) and 1(b), and using magnesium methylate, the corresponding magnesium complex is obtained. When starting from methyl silicate, the reaction yield is quantitative (95–100%).

EXAMPLE 4

Preparation of sodium bis(benzene-1,2-diolato)methylsilicate

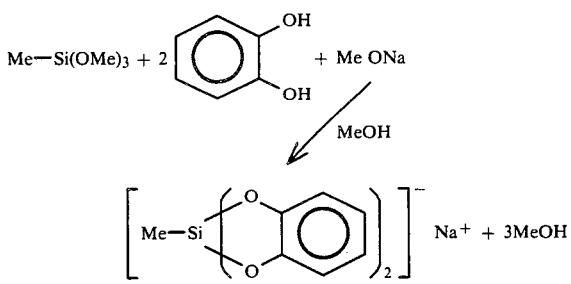

The preparation is carried out under nitrogen in a Schlenk tube with degassed solvents.

1.09 g of sodium (0.0475 mol) are dissolved in 15 ml of methanol. 6.47 g of $MeSi(OMe)_3$ (0.0475 mol) diluted in 10 ml of methanol are added rapidly at room temperature. A solution of 10.34 g of pyrocatechol (0.094 mol) in 20 ml of methanol is then added dropwise at room temperature. The reaction mixture is heated for about 4 hours at 45° C. The methanol is driven off in vacuo. The complex is then washed twice with ether under nitrogen to remove the unreacted pyrocatechol and $MeSi(OMe)_3$. The solution is filtered under nitrogen. The complex is dried in vacuo at 100° C. for one day to remove the ether. This gives 12 g of complex (yield 90%). The complex, obtained in the form of a powder, must be kept under nitrogen. It is soluble in methanol and DMSO. Spectral characteristics (TMS standard): $^{13}C$ NMR $(CD_3OD)$ 4 signals: $\delta=151.6$; 120.8; 113.2; 1.2 ppm. $^{29}Si$ NMR $(CD_3OD)\delta=-73.7$ ppm.

EXAMPLE 5

Preparation of potassium bis(benzene-1,2-diolato)methylsilicate

By following a procedure identical to that of Example 1, the air-stable complex of the formula:

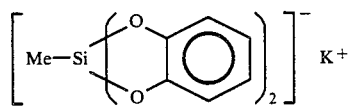

is obtained from potassium methylate.

EXAMPLE 6

Preparation of potassium bis(benzene-1,2-diolato)vinylsilicate

By following a procedure identical to that of Example 1, the air-stable complex of the formula:

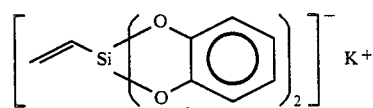

is obtained from $Si(OMe)_3$ and MeOK.

EXAMPLE 7

Preparation of sodium bis(benzene-1,2-diolato)phenylsilicate

By following a procedure identical to that of Example 1, the stable complex of the formula:

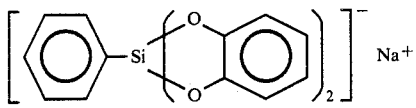

is obtained from

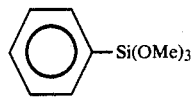

and MeONa.

EXAMPLE 8

Preparation of sodium bis(benzene-1,2-diolato)benzylsilicate

By following a procedure identical to that of Example 1, the air-stable complex of the formula:

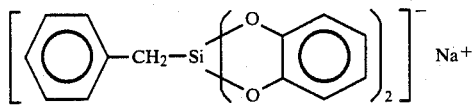

is obtained from

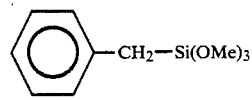

and MeONa.

EXAMPLE 9

Preparation of sodium bis(benzene-1,2-diolato)(naphth-1-yl)silicate

By following a procedure identical to that of Example 1, the stable complex of the formula:

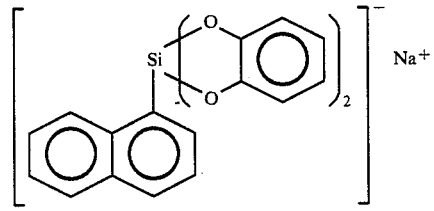

is obtained from

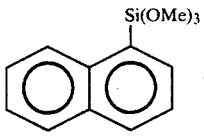

and MeONa.

EXAMPLE 10

Reduction of sodium bis(benzene-1,2-diolato)-α-naphthylsilicate with LiAlH$_4$

The reactions are carried out under nitrogen with degassed reactants and solvents.

7.88 g of sodium bis(benzene-1,2-diolato)-α-naphthylsilicate (20 mmol) are suspended in 50 ml of anhydrous ether and added to a suspension of 2 g of LiAlH$_4$ (52 mmol) in 30 ml of anhydrous ether. The reaction medium is left at room temperature for 4 hours, with stirring. It is hydrolyzed with HCl (4N). The aqueous phase is extracted 3 times with ether. The combined ether phases are washed with sodium hydroxide solution to remove the pyrocatechol, with water and with saturated sodium chloride solution until the washings are neutral, and then dried over MgSO$_4$. 2.3 g of α-naphthylsilane (yield 73%) are obtained after distillation. Boiling point: 135°–140°/25 mm Hg.

EXAMPLE 11

Reduction of sodium bis(benzene-1,2-diolato)phenylsilicate with LiAlH$_4$

By following the procedure of Example 10, starting from 6.88 g of sodium bis(benzene-1,2-diolato)phenylsilicate (20 mmol), 1.5 g of phenylsilane are obtained (yield 72%). Boiling point: 120°/760 mm Hg.

EXAMPLE 12

Reduction of sodium bis(benzene-1,2-diolato)phenylsilicate with NaH/Et$_3$Al

The reactions are carried out under nitrogen with degassed reactants and solvents.

The Et$_3$Al/NaH complex is prepared by adding 2.01 g of NaH as an 80% suspension in oil (66 mmol) to 75 ml of a 0.6M solution of Et$_3$Al in hexane (45 mmol). This mixture is stirred for ¼ hour at room temperature. It is then cooled to 0° C. and a suspension of 5.16 g of sodium bis(benzene-1,2-diolato)phenylsilicate (15 mmol) in 50 ml of anhydrous hexane is added. The reaction mixture is then left to stand for 1 hour at room temperature, with stirring. After this time, the medium is clear and a gray gum is stuck to the bottom of the Schlenk tube. It is hydrolyzed in the cold very slowly with 4N HCl until the pH is acid. Extraction is carried out with hexane and the extract is washed with water until the washings are neutral. It is dried over MgSO$_4$. 0.97 g of phenylsilane (yield 60%) is obtained after distillation.

Note: This yield can be improved because part of the phenylsilane is entrained by the hexane.

EXAMPLE 13

Reduction of sodium bis(benzene-1,2-diolato)-α-naphthylsilicate with NaH/Et₃Al

By following the procedure of Example 12, starting from 4 g of sodium bis(benzene-1,2-diolato)-α-naphthylsilicate (10 mmol), 1.02 g of α-naphthylsilane are obtained (yield 65%).

EXAMPLE 14

Reduction of sodium bis(benzene-1,2-diolato)phenylsilicate with diisobutylaluminum hydride The reaction is carried out under nitrogen with degassed reactants and solvents.

100 ml of a M solution of diisobutylaluminum hydride in hexane (100 mmol) are cooled to 0° C. A suspension of 6.88 g of sodium bis(benzene-1,2-diolato)phenylsilicate (20 mmol) in methylene chloride is added. The reaction medium is stirred for 4 hours at room temperature (test: there is an excess of hydride). It is then hydrolyzed with 4N HCl (very violent reaction in the cold) until the pH is acid. The medium is extracted with methylene chloride. The combined organic phases are washed with sodium hydroxide solution to remove the pyrocatechol, and then with water and with saturated sodium chloride solution until the washings are neutral. The organic solution is dried over MgSO₄.

1.4 g of phenylsilane (yield 65%) are obtained after distillation. Boiling point: 120°/760 mm Hg.

Note: When the solvent is removed at atmospheric pressure, a considerable quantity of phenylsilane is entrained (monitoring by GC). The yield observed can therefore be improved.

What is claimed is:

1. A process for the preparation of hydrogenosilanes or halogenosilanes of the general formula I:

R—SiR'₃     (I)

in which:

R represents a hydrogen or chlorine atom or an alkyl, alkenyl, alkynyl, aryl, aralkyl, aralkenyl, aralkynyl or alkylaryl radical in which the aliphatic fragments are linear, branched or cyclic and contain from 1 to 20 carbon atoms, and R' represents a hydrogen or chlorine atom, which comprises reacting a silicon complex corresponding to the general formula II:

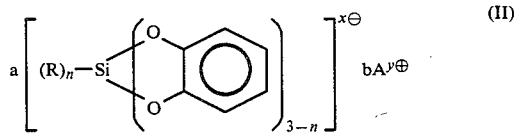

(II)

in which:

R represents an alkyl, alkenyl, alkynyl, aryl, aralkyl, aralkenyl, aralkynyl or alkylaryl radical in which the aliphatic fragments are linear, branched or cyclic and contain from 1 to 20 carbon atoms, A represents an alkali metal or alkaline earth metal, n = 0 or 1 and a, b, x and y = 1 or 2, with the proviso that:

when n = 0, x = 2 when n = 1, x = 1 and satisfying the equation of electrical neutrality:

$ax = by$.

with a reducing agent or a halogen-containing oxidizing agent in an anhydrous solvent medium and under an inert atmosphere, and then carrying out acid hydrolysis and extracting the said compound of the formula I.

2. The process as claimed in claim 1, wherein a hexacoordinate silicon complex of the general formula IIa:

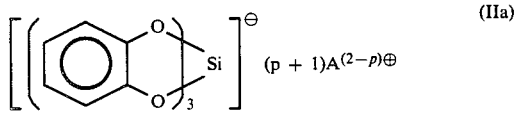

(IIa)

in which:

A represents an alkali metal or alkaline earth metal and p = 0 or 1, is used.

3. The process as claimed in claim 1, wherein a pentacoordinate silicon complex of the general formula IIb:

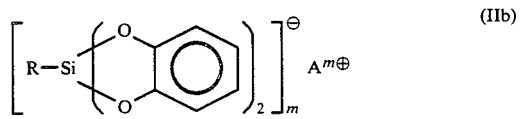

(IIb)

in which:

R denotes an alkyl, alkenyl, alkynyl, aryl, aralkyl, aralkenyl, aralkynyl or alkylaryl radical in which the aliphatic fragments are linear, branched or cyclic and contain from 1 to 20 carbon atoms, A represents an alkali metal or alkaline earth metal and m = 1 or 2, is used.

4. The process as claimed in claim 1, wherein the reducing agent is chosen from hydrides such as lithium aluminum hydride, diisobutylaluminum hydride and sodium hydride associated with a trialkylaluminum compound, especially triethylaluminum.

5. The process as claimed in claim 1, wherein the halogen-containing oxidizing agent is chosen from the group comprising chlorine, hydrochloric acid, PCl₃, PCl₅, POCl₃ and SOCl₂.

* * * * *